United States Patent
Arnin

(10) Patent No.: US 9,078,703 B2
(45) Date of Patent: Jul. 14, 2015

(54) SPINAL ROD HAVING A POST-OPERATIVE ADJUSTABLE DIMENSION

(75) Inventor: Uri Arnin, Kiryat Tivon (IL)

(73) Assignee: SPINE21 LTD., Haifa (IL)

( * ) Notice: Subject to any disclaimer, the term of this patent is extended or adjusted under 35 U.S.C. 154(b) by 170 days.

(21) Appl. No.: 13/511,431

(22) PCT Filed: Nov. 5, 2010

(86) PCT No.: PCT/US2010/055533
§ 371 (c)(1),
(2), (4) Date: May 23, 2012

(87) PCT Pub. No.: WO2011/066078
PCT Pub. Date: Jun. 3, 2011

(65) Prior Publication Data
US 2012/0283781 A1    Nov. 8, 2012

Related U.S. Application Data

(60) Provisional application No. 61/272,969, filed on Nov. 25, 2009.

(51) Int. Cl.
*A61B 17/70* (2006.01)
*A61B 17/00* (2006.01)

(52) U.S. Cl.
CPC ......... *A61B 17/7016* (2013.01); *A61B 17/7017* (2013.01); *A61B 2017/00734* (2013.01)

(58) Field of Classification Search
CPC .......... A61B 17/7014; A61B 17/7016; A61B 17/7017

USPC .................. 606/258–260, 105, 53–57, 62–68
See application file for complete search history.

(56) References Cited

U.S. PATENT DOCUMENTS

| | | | | |
|---|---|---|---|---|
| 2,702,031 | A | * | 2/1955 | Wenger ........................... 606/51 |
| 4,078,559 | A | * | 3/1978 | Nissinen ........................ 606/258 |
| 4,308,863 | A | * | 1/1982 | Fischer ........................... 606/57 |
| 4,401,112 | A | * | 8/1983 | Rezaian ......................... 606/279 |
| 4,445,513 | A | * | 5/1984 | Ulrich et al. ................. 606/86 A |

(Continued)

FOREIGN PATENT DOCUMENTS

| | | |
|---|---|---|
| DE | 202007009970 | 9/2007 |
| WO | 01/78614 | 10/2001 |

OTHER PUBLICATIONS

English translation of Description: DE 20 2007 009 970 U1, European Patent Office, generated Feb. 6, 2014,<www.epo.org>, 13 pages.*

(Continued)

*Primary Examiner* — Eduardo C Robert
*Assistant Examiner* — Jacqueline Johanas
(74) *Attorney, Agent, or Firm* — Dekel Patent Ltd.; David Klein

(57) ABSTRACT

A spinal implant (200) including first spinal attachment member (201) for attaching to a first spinal portion, second spinal attachment member (202) for attaching to a second spinal portion, and a post-implantation variable dimension rod disposed between the first and second spinal attachment members, which is operable after completing surgery in which said spinal implant was installed into a patient, to cause relative movement between the first and second spinal attachment members.

13 Claims, 4 Drawing Sheets

(56) References Cited

U.S. PATENT DOCUMENTS

| | | | |
|---|---|---|---|
| 4,611,582 A * | 9/1986 | Duff | 606/258 |
| 4,657,550 A * | 4/1987 | Daher | 623/17.11 |
| 4,658,809 A * | 4/1987 | Ulrich et al. | 606/258 |
| 4,771,767 A * | 9/1988 | Steffee | 606/256 |
| 4,931,055 A * | 6/1990 | Bumpus et al. | 606/60 |
| 5,330,472 A * | 7/1994 | Metz-Stavenhagen | 606/53 |
| 5,336,223 A * | 8/1994 | Rogers | 606/258 |
| 5,387,212 A * | 2/1995 | Yuan et al. | 606/264 |
| 5,413,602 A * | 5/1995 | Metz-Stavenhagen | 623/17.15 |
| 5,437,669 A * | 8/1995 | Yuan et al. | 606/278 |
| 5,458,641 A * | 10/1995 | Ramirez Jimenez | 623/17.11 |
| 5,468,241 A * | 11/1995 | Metz-Stavenhagen et al. | 606/319 |
| 5,490,851 A * | 2/1996 | Nenov et al. | 606/252 |
| 5,575,790 A * | 11/1996 | Chen et al. | 606/60 |
| 5,613,968 A * | 3/1997 | Lin | 606/320 |
| 5,667,506 A * | 9/1997 | Sutterlin | 606/252 |
| 5,702,392 A * | 12/1997 | Wu et al. | 606/264 |
| 5,702,455 A * | 12/1997 | Saggar | 623/17.15 |
| 5,704,939 A * | 1/1998 | Justin | 606/63 |
| 5,916,267 A * | 6/1999 | Tienboon | 623/17.11 |
| 5,989,290 A * | 11/1999 | Biedermann et al. | 623/17.11 |
| 6,755,828 B2 * | 6/2004 | Shevtsov et al. | 606/54 |
| 6,916,319 B2 * | 7/2005 | Munting | 606/278 |
| 7,588,579 B2 * | 9/2009 | Mommaerts | 606/105 |
| 7,628,799 B2 * | 12/2009 | Richelsoph et al. | 606/250 |
| 7,708,765 B2 * | 5/2010 | Carl et al. | 606/279 |
| 7,763,053 B2 * | 7/2010 | Gordon | 606/258 |
| 7,981,118 B2 * | 7/2011 | Mommaerts | 606/105 |
| 7,981,157 B2 * | 7/2011 | Castleman et al. | 623/17.15 |
| 8,211,149 B2 * | 7/2012 | Justis | 606/258 |
| 8,292,963 B2 * | 10/2012 | Miller et al. | 623/17.16 |
| 8,382,756 B2 * | 2/2013 | Pool et al. | 606/54 |
| 8,439,914 B2 * | 5/2013 | Ross et al. | 606/56 |
| 8,585,740 B1 * | 11/2013 | Ross et al. | 606/258 |
| 8,641,723 B2 * | 2/2014 | Connor | 606/105 |
| 2003/0144665 A1 * | 7/2003 | Munting | 606/61 |
| 2004/0030395 A1 * | 2/2004 | Blunn et al. | 623/18.12 |
| 2005/0080420 A1 * | 4/2005 | Farris et al. | 606/61 |
| 2006/0036259 A1 * | 2/2006 | Carl et al. | 606/90 |
| 2006/0047282 A1 * | 3/2006 | Gordon | 606/61 |
| 2006/0200130 A1 * | 9/2006 | Hawkins et al. | 606/61 |
| 2007/0255407 A1 * | 11/2007 | Castleman et al. | 623/17.11 |
| 2007/0270803 A1 * | 11/2007 | Giger et al. | 606/60 |
| 2008/0172063 A1 * | 7/2008 | Taylor | 606/105 |
| 2009/0036892 A1 * | 2/2009 | Karidis et al. | 606/60 |
| 2009/0093820 A1 * | 4/2009 | Trieu et al. | 606/103 |
| 2009/0112262 A1 * | 4/2009 | Pool et al. | 606/246 |
| 2009/0112263 A1 * | 4/2009 | Pool et al. | 606/246 |
| 2009/0125062 A1 | 5/2009 | Arnin | |
| 2009/0275984 A1 | 11/2009 | Kim | |
| 2009/0281542 A1 * | 11/2009 | Justis | 606/60 |
| 2009/0306717 A1 * | 12/2009 | Kercher et al. | 606/258 |
| 2010/0100130 A1 * | 4/2010 | Carl et al. | 606/264 |
| 2010/0151402 A1 * | 6/2010 | Williams | 433/7 |
| 2010/0198261 A1 * | 8/2010 | Trieu et al. | 606/264 |
| 2010/0217271 A1 * | 8/2010 | Pool et al. | 606/90 |
| 2010/0331840 A1 * | 12/2010 | Ross et al. | 606/54 |
| 2011/0190820 A1 * | 8/2011 | Johansson et al. | 606/264 |
| 2011/0196371 A1 * | 8/2011 | Forsell | 606/62 |
| 2011/0196435 A1 * | 8/2011 | Forsell | 606/86 R |
| 2012/0259332 A1 * | 10/2012 | Bulloch et al. | 606/57 |
| 2013/0253513 A1 * | 9/2013 | Ross et al. | 606/56 |

OTHER PUBLICATIONS

PCT Search PCT/US2010/055533, mailed Oct. 3, 2011, 3 pages.

\* cited by examiner

SPINAL ROD HAVING A POST-OPERATIVE ADJUSTABLE DIMENSION

CROSS-REFERENCE TO RELATED APPLICATIONS

This application claims priority under 35 USC §119 to U.S. Provisional Patent Application, Ser. No. 61/272969, filed Nov. 25, 2009.

FIELD OF THE INVENTION

The present invention relates generally to spinal implants and prostheses, and particularly to a spinal fusion cage having a post-operative adjustable dimensions.

BACKGROUND OF THE INVENTION

Spinal implants with the capability of height adjustment are known. One device is shown and described in PCT Patent Application PCT/IL2008/001423 (WO 2009/060427), to the present applicant. One of the devices shown therein uses an inclined, threaded interface between first and second support plates, as is now described with reference to FIG. 1.

A spinal implant 20 includes a post-implantation variable dimension device 22, and is connected to pedicle screws 24 (spinal attachment members 24). Actuation of variable dimension device 22 changes the distance between screws 24. Post-implantation variable dimension device 22 includes a post arranged for linear motion, such as by means of a miniature linear actuator which is remote controlled.

SUMMARY OF THE INVENTION

The present invention seeks to provide an improved spinal rod (or implant, or prosthesis, the terms being used interchangeably) having a post-operative adjustable dimensions, to be placed between two adjacent vertebras, with the ability to adjust the distance between the vertebras.

In one embodiment, at least one of its dimensions of the spinal implant can be modified post-implantation by means of remote control.

The adjustment of the length of the spinal rod, can be electrically powered, such as by an electric motor (powered by a battery or remote induction), and controlled via remote control.

The prosthesis is configured to bridge between two vertebrae, most preferably but not limited to, adjacent vertebrae. The prosthesis includes a plurality of attachment members (end features) configured to be attached to a plurality of bone attachment points, such as but not limited to, vertebral pedicles.

There is thus provided in accordance with a non-limiting embodiment of the present invention a spinal implant including first spinal attachment member for attaching to a first spinal portion, second spinal attachment member for attaching to a second spinal portion, and a post-implantation variable dimension rod disposed between the first and second spinal attachment members, which is operable after completing surgery in which said spinal implant was installed into a patient, to cause relative movement between the first and second spinal attachment members.

In accordance with an embodiment of the present invention the first and second spinal attachment members include pedicle screws.

In accordance with an embodiment of the present invention the post-implantation variable dimension device changes a distance between the first and second spinal attachment members.

In accordance with an embodiment of the present invention the post-implantation variable dimension device is connected to mechanical elements connected to rods attached to the pedicle screws.

In accordance with an embodiment of the present invention the post operative adjusted rod includes a rotating element having at least one internal thread and at least one shaft engaged with this thread. The rotating element and the shaft are disposed between the attachment members such that when the rotating element is turned the shaft moves in or out, thereby changing the distance of first attachment member from the second attachment member.

In accordance with an embodiment of the present invention the rotating element has two threads in two different directions, left and right, and two threaded shafts are engaged in these threads.

In accordance with an embodiment of the present invention the post-implantation variable dimension rod is hydraulically or pneumatically operated.

In accordance with an embodiment of the present invention the post-implantation variable dimension device is electrically operated.

In accordance with an embodiment of the present invention the post-implantation variable dimension rod includes an internal, implanted portion. The internal portion may include at least one of a piston, a pump, a microprocessor, an RF emitter/transmitter, an LVDT (linear variable differential transducer), a strain sensor, an electric coil, a battery, and a capacitor.

In accordance with an embodiment of the present invention the post-implantation variable dimension rod includes an external control portion. The external control portion may include at least one of a control panel, a processor, an RF transmitter/emitter, a magnetic power source, an electric coil and a cellular communication device. The communication between the external control portion and the implanted portion may be controlled by a code or password to protect against undesired operation of the internal device.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1:
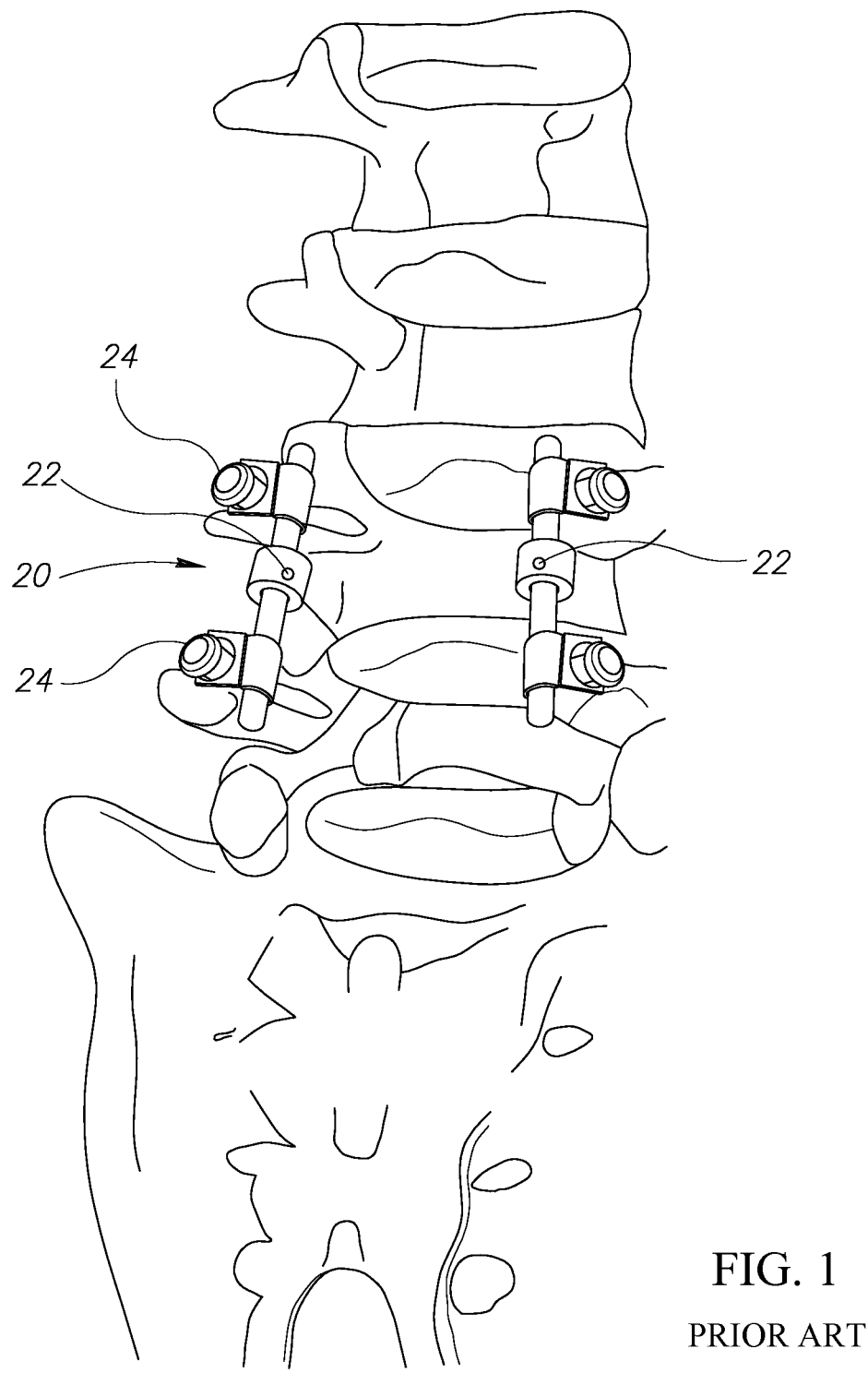
FIG. 1 is a simplified pictorial illustration of a prior art spinal implant including a post-implantation variable dimension device, connected to pedicle screws so that actuating the variable dimension mechanism can change the distance between the screws.
Figure 2:
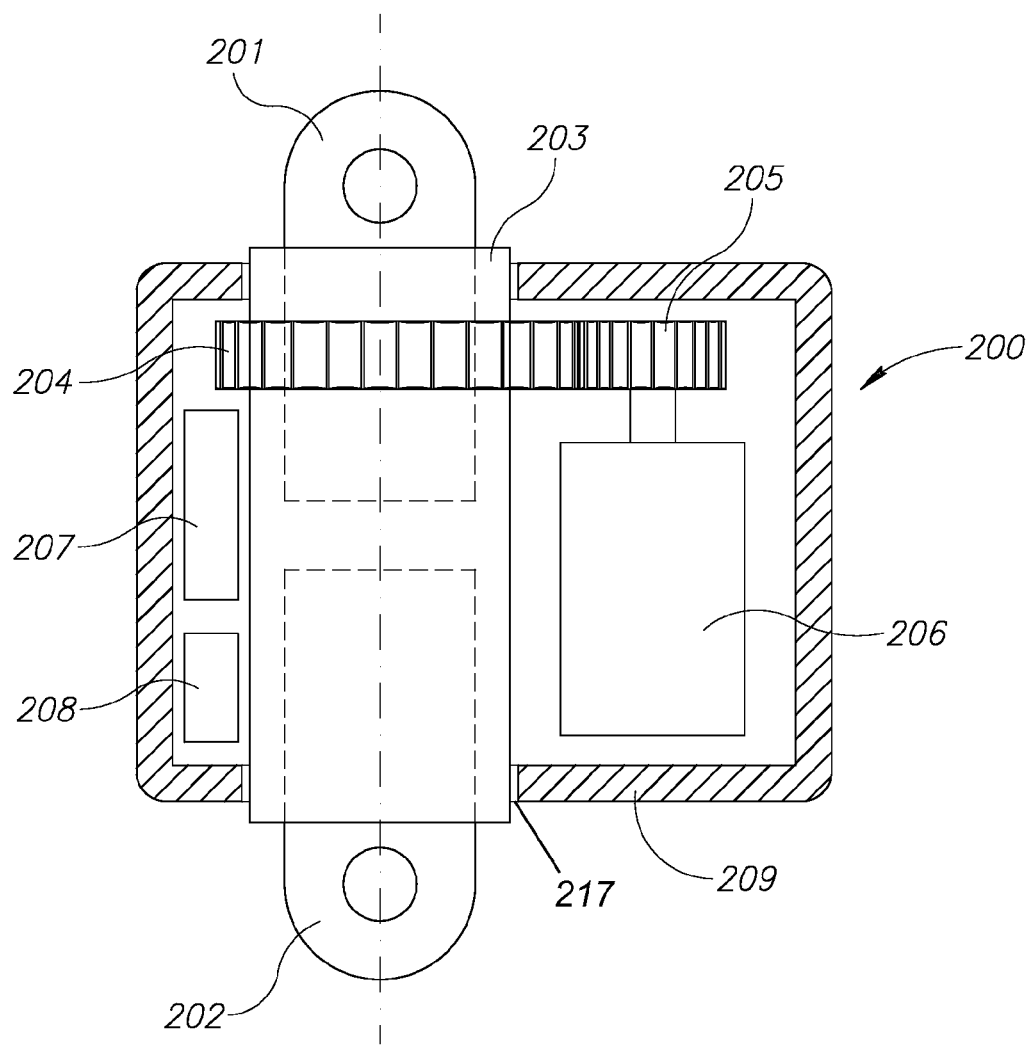
FIG. 2 is a simplified semi-cross section pictorial illustration of a spinal implant including a post-implantation variable dimension rod, constructed and operative in accordance with an embodiment of the invention.

Reference is now made to FIG. 2, which illustrates a spinal implant 200, constructed and operative in accordance with a non-limiting embodiment of the invention.

Spinal implant 200 includes a first (e.g., upper) rod 201 and a second (e.g., lower) rod 202 both threadingly received in a sleeve 203 mounted in a housing 209. The threaded connection between sleeve 203 and first rod 201 is opposite in direction to the threaded connection between sleeve 203 and second rod 202; one is right-handed, the other left-handed. In this manner, rotating sleeve 203 in one direction (e.g., clockwise) causes the rods to move apart whereas rotating sleeve 203 in the opposite direction causes the rods to move towards each other, when the rods are connected to different spinal structure. (The term "spinal structure" encompasses not just anatomical parts of the spine, but also spinal mounting structure, such as, but not limited to, cross-connector rods or pedicle screws and the like). Sleeve 203 may be journaled in bearings 217 in housing 209.

Both first and second rods 201 and 202 each have mounting structure 215 (e.g., mounting holes or lugs) at distal ends thereof for attaching to spinal structure.

A gear 204 is connected to, or can be part of, the outer contour of sleeve 203. A gear train 205 is disposed between gear 204 and an actuating motor 206. In accordance with an embodiment of the present invention the gear system 204-205 can be a spur gear, worm gear, belt, chain or other known mechanisms to transmit motion. Actuating motor 206 rotates sleeve 203 through a pre-designed gear ratio and rods 201 and 202 move with respect to one other. Motor 206 can be controlled by a printed circuit 208, which may include, without limitation, at least one of a micro-controller, radio system, remote switch, capacitor, and induction coil. The power source to activate the motor can be a battery 207. The electrical components may be controlled by an external unit via remote control (radio, light, voice etc).

Figure 6:
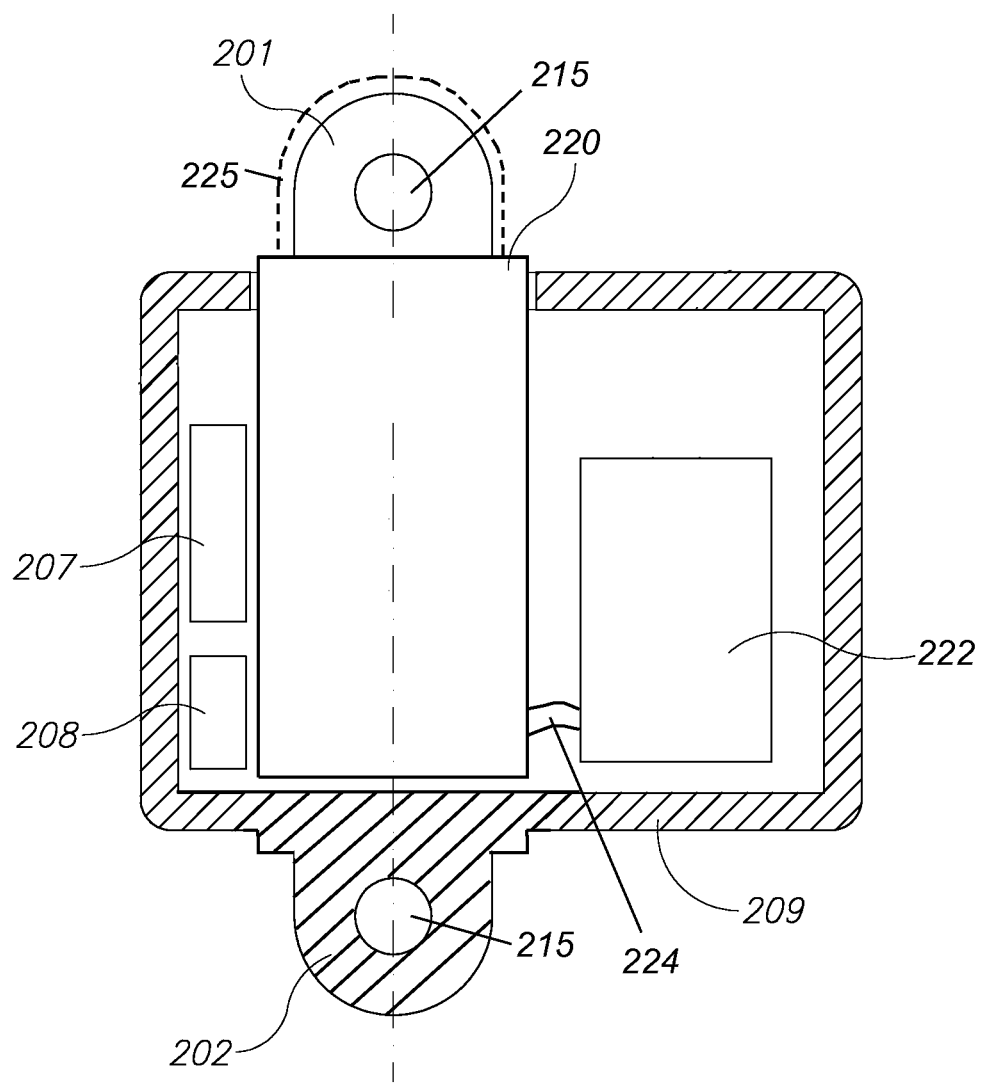
FIG. 6 is a simplified pictorial illustration of an arrangement of rods and pedicle screws, including a post-implantation variable dimension rod, constructed and operative in accordance with still another embodiment of the invention.

Alternatively, as shown in the embodiment of FIG. 6, second rod 202 does not have to be moved by the actuating motor. Instead, second rod 202 can be attached to, or part of, housing 209. The actuating motor moves first rod 201 towards or away from second rod 202.

Instead of being electrically actuated, actuating motor 206 can be hydraulic or pneumatic, and this option is illustrated in FIG. 6. Actuating motor 206 includes a fluid-operated (hydraulic or pneumatic) piston 220 operated by a fluid (hydraulic or pneumatic) pump 222, connected thereto by a tube 224.

FIG. 6 also shows the option that at least one of the rods 201 or 202 may be connected directly to a bone (e.g., pedicle) screw 225 inserted at mounting structure 215.

Figure 3:
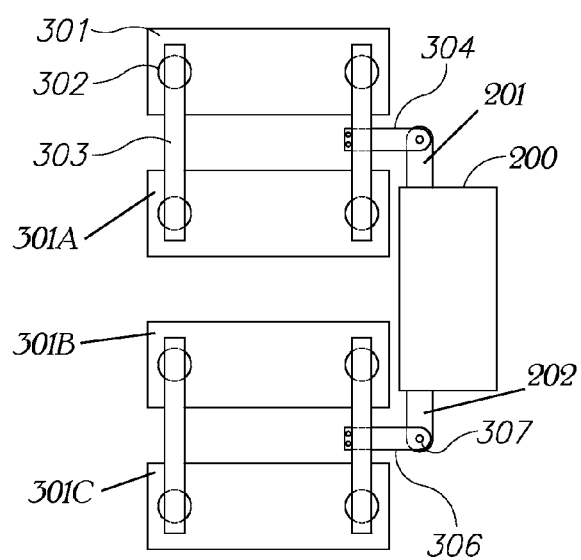
FIG. 3 is a simplified pictorial illustration of one arrangement of rods and pedicle screws, including a post-implantation variable dimension rod, constructed and operative in accordance with an embodiment of the invention.

Reference is now made to FIG. 3, which illustrates one option of connecting the post operative adjustable rods 201 and 202, as described in FIG. 2, to spinal structure.

In this illustrated embodiment, the spinal structure includes a first vertebral body 301 and three other vertebral bodies below body 301, labeled 301A, 301B and 301C. Two pedicle screws 302 are inserted in each vertebral body. An intervertebral rod 303 connects pedicle screws of adjacent vertebral bodies 301 and 301A, as well as 301B and 301C. There are thus four rods shown. Different types of bone screws, inserted in different locations into the vertebra, can be used.

First rod 201 of spinal implant 200 is connected to a first attachment member 304 and a second attachment member 305 is attached to second rod 202 via attachment junctions 307 placed at mounting structures 215. The attachment junctions 307 between the rods and the attachment members may include, without limitation, a rotatable hinge, a spherical joint, a fixed rigid attachment or any other way known to those skilled in the art. First and second attachment members 304 and 305 are connected to intervertebral rods 303 between adjacent vertebral bodies.

Figure 4:
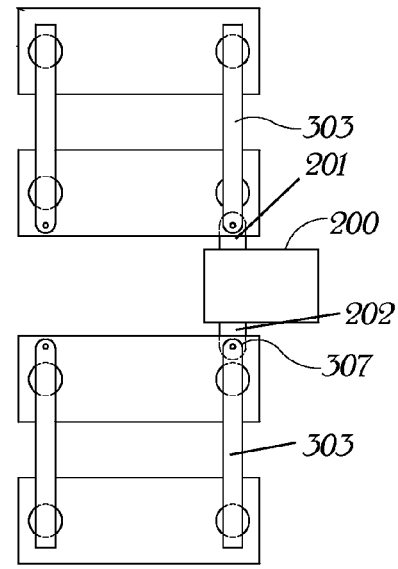
FIG. 4 is a simplified pictorial illustration of an arrangement of rods and pedicle screws, including a post-implantation variable dimension rod, constructed and operative in accordance with another embodiment of the invention.

Reference is now made to FIG. 4, which illustrates another option of connecting the post operative adjustable rods to spinal structure. In this embodiment, first and second rods 201 and 202 of spinal implant 200 are connected to first and second ends of adjacent intervertebral rods 303 via attachment junctions 307.

Figure 5:
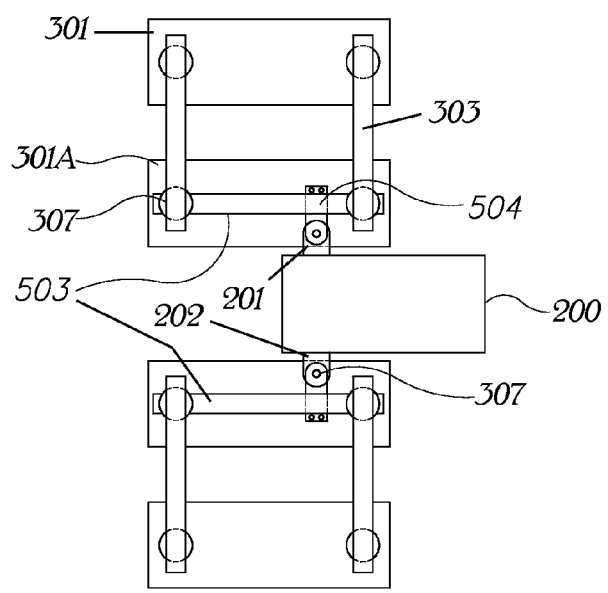
FIG. 5 is a simplified pictorial illustration of an arrangement of rods and pedicle screws, including a post-implantation variable dimension rod, constructed and operative in accordance with yet another embodiment of the invention.

Reference is now made to FIG. 5, which illustrates yet another option of connecting the post operative adjustable rods to spinal structure. In this embodiment, first and second rods 201 and 202 of spinal implant 200 are connected to first and second cross-connector rods 503 with link members 504 via attachment junctions 307. The cross-connector rods 503 are connected to left and right intervertebral rods 303 via attachment junctions 307.

It is noted that in FIGS. 3-6 only one post operative variable dimension spinal implant 200 is shown. However, more than one implant can be used in the same segment (e.g. between L4 and L5) or above and below the segments.

The embodiments of FIGS. 3-6 can be interchanged and/or integrated with one another in different combinations.

What is claimed is:
1. A spinal implant comprising:
a first rod and a second rod both threadingly received in a sleeve mounted in a housing, wherein a threaded connection between said sleeve and said first rod is opposite in direction to a threaded connection between said sleeve and said second rod, wherein said first and second rods each have mounting structure at distal ends thereof for attaching to spinal structure; and
an actuating motor, disposed in said housing and non-concentric with said sleeve, operative to rotate said sleeve through a gear system, wherein rotating said sleeve in one direction causes said first and second rods to move apart whereas rotating said sleeve in an opposite direction causes said first and second rods to move towards each other, wherein the threaded connection between said sleeve and said first rod and the threaded connection between said sleeve and said second rod are both formed in a common bore in said sleeve, and wherein said sleeve is structured to permit said first and second rods to abut against each other.

2. The spinal implant according to claim 1, wherein said actuating motor is controlled by a printed circuit, which comprises at least one of a micro-controller, radio system, remote switch, capacitor, and induction coil.

3. The spinal implant according to claim 1, wherein said first rod is connected to a first attachment member via an attachment junction placed at said mounting structure.

4. The spinal implant according to claim 3, wherein said second rod is connected to a second attachment member via an attachment junction placed at said mounting structure at the distal end of said second rod.

5. The spinal implant according to claim 4, wherein said first and second attachment members are connected to intervertebral rods adapted for attachment between vertebral bodies.

6. The spinal implant according to claim 4, wherein said first rod and said second rod are connected to first and second ends of intervertebral rods via said attachment junctions placed at said mounting structures.

7. The spinal implant according to claim 4, wherein said first rod and said second rod are connected to first and second cross-connector rods with link members via said attachment junctions placed at said mounting structures.

8. The spinal implant according to claim 7, wherein said cross-connector rods are connected to left and right intervertebral rods via said attachment junctions.

9. The spinal implant according to claim 1, wherein at least one of said first and second rods is connected directly to a bone screw inserted at said mounting structure.

10. The spinal implant according to claim 1, wherein said sleeve is journaled in bearings in said housing.

11. The spinal implant according to claim 1, wherein said gear system comprises a gear connected to or part of an outer contour of said sleeve.

12. The spinal implant according to claim 1, wherein said common bore has a constant cross section.

13. The spinal implant according to claim 1, wherein a portion of said gear system is non-concentric with said sleeve.

\* \* \* \* \*